US009983200B2

(12) United States Patent
Pavan et al.

(10) Patent No.: US 9,983,200 B2
(45) Date of Patent: May 29, 2018

(54) COMPOSITIONS AND METHODS FOR PREDICTING AGE OF ONSET OF A LYSOSOMAL STORAGE DISEASE OR A DISEASE ASSOCIATED WITH A LYSOSOMAL DEFECT

(71) Applicant: The United States of America, as represented by the Secretary, Department of Health & Human Services, Washington, DC (US)

(72) Inventors: William J. Pavan, Derwood, MD (US); Jorge L. Rodriguez, Bethesda, MD (US); Denise M. Larson, Bethesda, MD (US); Forbes D. Porter, III, Gaithersburg, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 0 days. days.

(21) Appl. No.: 14/776,440

(22) PCT Filed: Mar. 14, 2014

(86) PCT No.: PCT/US2014/028986
§ 371 (c)(1),
(2) Date: Sep. 14, 2015

(87) PCT Pub. No.: WO2014/153083
PCT Pub. Date: Sep. 25, 2014

(65) Prior Publication Data
US 2016/0025712 A1 Jan. 28, 2016

Related U.S. Application Data

(60) Provisional application No. 61/781,807, filed on Mar. 14, 2013.

(51) Int. Cl.
*A01N 43/04* (2006.01)
*G01N 33/53* (2006.01)
*G01N 33/567* (2006.01)
*G01N 33/52* (2006.01)
*G01N 33/58* (2006.01)
*G01N 33/68* (2006.01)

(52) U.S. Cl.
CPC ........... *G01N 33/52* (2013.01); *G01N 33/582* (2013.01); *G01N 33/6893* (2013.01); *G01N 33/6896* (2013.01); *G01N 2500/10* (2013.01); *G01N 2800/04* (2013.01); *G01N 2800/2821* (2013.01); *G01N 2800/2835* (2013.01); *G01N 2800/52* (2013.01)

(58) Field of Classification Search
None
See application file for complete search history.

(56) References Cited

U.S. PATENT DOCUMENTS

| 5,223,409 A | 6/1993 | Lardner et al. |
| 6,759,189 B1 | 7/2004 | Meikle et al. |
| 2010/0093004 A1 | 4/2010 | Patton et al. |

FOREIGN PATENT DOCUMENTS

| WO | WO-2013072060 A2 | 5/2013 |
| WO | WO-2013090857 A1 | 6/2013 |

OTHER PUBLICATIONS

Wijburg et al. (2012) Neurology. Development of a suspicion index to aid diagnosis of Niemann-Pick disease type C. May 15;78(20):1560-7.
Porter et al. (2010). Cholesterol oxidation products are sensitive and specific blood-based biomarkers for Niemann-Pick C1 disease. Sci Transl Med. Nov. 3; 2(56): 56-81.
Nicole M. Yanjanin et al: "Linear clinical progression, independent of age of onset, in Niemann-Pick disease, type C", American Journal of Medical Genetics Part B: Neuropsychiatric Genetics, vol. 9999B, No. 1, Jan. 1, 2010 (Jan. 1, 2010), pp. n/a-n/a.
F. M. Platt et al: "The cell biology of disease: Lysosomal storage disorders: The cellular impact of lysosomal dysfunction", Science, vol. 334, No. 6056, Nov. 26, 2012 (Nov. 26, 2012), pp. 678-734.
C:"Contents",, Jan. 1, 2012 (Jan. 1, 2012), pp. 1-43.
Lachmann Robin H et al: "Treatment with miglustat reverses the lipid-trafficking defect in Niemann-Pick disease type C", Neurobiology of Disease, Blackwell Scientific Publications, Oxford, GB, vol. 16, No. 3, Aug. 1, 2004 (Aug. 1, 2004), pp. 654-658.
Anderson, et al., "A View of Acidic Intracellular Compartments," J. Cell Biol., vol. 106, pp. 539-543, Mar. 1988.
Barasch, et al., "Defective Acidification of Intracellular Organelles in Cystic Fibrosis," Nature vol. 352, pp. 70-73, Jul. 1991.
Carell, et al., "A Solution-phase Screening Procedure for the Isolation of Active Compounds from a Library of Molecules," Angew. Chem. Int. Ed. Engl. 33, pp. 2061-2064, 1994.
Carrell, et al., "A novel Procedure for the Synthesis of Libraries Containing Small Organic Molecules," Angew. Chem. Int. Ed. Engl. 33, pp. 2059-2061, 1994.
Cho, et al., "An Unnatural Biopolymer," Science vol. 261, pp. 1303-1305, Sep. 1993.
Cull, et al., "Screening for Receptor Ligands Using Large Libraries of Peptides Linked to the C Terminus of the *lac*Repressor," Proc. Natl. Acad. Sci. USA, vol. 89, pp. 1865-1869, Mar. 1992.
Cwirla, et al., "Peptides on Phage: A Vast Library of Peptides for Identifying Ligands," Proc. Natl. Acad. Sci. USA, vol. 87, pp. 6378-6382, Aug. 1990.
Deernick, et al., "Fluorescence Photooxidation with Eosin: a Method for High Resolution Immunolocalization and In Situ Hybridization Detection for Light and Electron Microscopy", J. Cell Biol., vol. 126, No. 4, pp. 901-910, Aug. 1994.
Dehay, B. et al., "Loss of P-type ATPase ATP13A2/PARK9 Function Induces General Lysosomal Deficiency and Leads to Parkinson Disease Neurodegeneration," Proc. Natl. Acad. Sci. 109 (2012) pp. 9611-9616.

(Continued)

*Primary Examiner* — Olga N Chernyshev
(74) *Attorney, Agent, or Firm* — Bryan D. Zerhusen; Locke Lord LLP

(57) ABSTRACT

The present invention features diagnostic compositions and methods for predicting the age of onset of a lysosomal storage disease or a disease associated with a lysosomal defect in subject.

12 Claims, 9 Drawing Sheets

(56) References Cited

OTHER PUBLICATIONS

Devlin, et al., "Random Peptide Libraries: A Source of Specific Protein Binding Molecules," Science, vol. 249, pp. 404-406, Jul. 1990.

DeWitt, et al., "Diversomers": An approach to nonpeptide, nonoligomeric chemical diversity, Proc. Natl. Acad. Sci. USA, vol. 90, pp. 6909-6913, Aug. 1993.

Diwu, Z., et al., "Novel Site-Selective Fluorescent Probes for Lysosome and Acidic Organelle Staining and Long-Term Tracking", International Society for Analytical Cytology: 1994 Abstracts—Cytometry suppl 7, 77 abstract #426B (1994).

Erb, et al., "Recursive Deconvolution of Combinatorial Chemical Libraries," Proc. Natl. Acad. Sci. USA, vol. 91, pp. 11422-11426, Nov. 1994.

Felici, J., "Selection of Antibody Ligands from a Large Library of Oligopeptides Expressed on a Multivalent Exposition Vector," J. Mol. Biol. 222, pp. 301-310, 1991.

Fodor, et al., "Multiplexed Biochemical Assays with Biological Chips," Nature vol. 364, pp. 555-556, Aug. 1993.

Gallop, et al., "Applications of Combinatorial Technologies to Drug Discovery. 1. Background and Peptide Combinatorial Libraries," J. Med. Chem. vol. 37, No. 9, pp. 1233-1251, Apr. 1994.

Griffiths, et al., The Mannose 6-phosphate Receptor and the Biogenesis of Lysosomes, Cell, vol. 52, pp. 329-341, Feb. 1988.

Huang, et al., "In Vivo Analysis of the Stability and Transport of Nuclear Poly(A)+RNA," J. Cell Biol., vol. 126, No. 4, pp. 877-899, Aug. 1994.

Jiang, Lw., et al., "Alkalinization of the Lysosomes is Correlated with *ras*Transformation of Murine and Human Fibroblasts," J Biol Chem vol. 265, No. 9, pp. 4775-4777, Mar. 1990.

Lam, et al., "A New Type of Synthetic Peptide Library for Identifying Ligand-Binding Activity," Nature Publishing Group vol. 354, pp. 82-84, Nov. 1991.

Neidle, S., et al., "Molecular Aspects of Anticancer Drug Action," Eds., Macmillian (1983) pp. 233-282.

Patterson, MC, et al., "Recommendations for the Diagnosis and Management of Niemann—Pick Disease type C: an update," Mol. Genet. Metab. vol. 106, (2012) pp. 330-344.

Rosenbaum, A.I., et al, "Endocytosis of Beta-Cyclodextrins is Responsible for Cholesterol Reduction in Niemann—Pick type C mutant cells," Proc. Natl. Acad. Sci. 107 (2010), pp. 5477-5482.

Schultz, M.L., et al., "Clarifying Lysosomal Storage Diseases," Trends Neurosciences, Aug. 2011, vol. 34, No. 8, pp. 401-410.

Scott, et al., "Searching for Peptide Ligands with an Epitope Library," Science 249, pp. 386-390, Jun. 1990.

Swaroop, M., et al., "Evaluation of Cholesterol Reduction Activity of Methyl-β-cyclodextrin Using Differentiated Human Neurons and Astrocytes," I. Biomol. Screen. 17 (2012), pp. 1243-1251.

Vanier, M.T., et al., "Niemann—Pick Disease Type C," Clin. Genet. 64 (2003), pp. 269-281.

Vanier, M.T., et al., "Niemann—Pick Disease Type C," Orphanet J. Rare Diseases (2010) 5:16.

Xu, M., et al., "δ-Tocopherol Reduces Lipid Accumulation in Niemann—Pick type C1 and Wolman Cholesterol Storage Disorders," J. Biol. Chem. 287 (2012), pp. 39349-39360.

Yanjanin, N.M., et al., "Linear Clinical Progression, Independent of Age of Onset, in Niemann—Pick disease, type C," Am. J. Med. Genet. B Neuropsychiatr. Genet. 153B (2010) 132-140, Jan. 2010.

Zhang, Y-Z, et al., "Novel Fluorescent Acidic Organelle-Selective Dyes and Mitochondrion-Selective Dyes That Are Well Retained During Cell Fixation and Permeabilization", Mol Biol Cell 5, 113a, abstract #653 (1994) (Sunday, Endosomes and Lysosomes (652-657).

Zuckermann et al., "Discovery of Nanomolar Ligands for 7-Transmembrane G-Protein-Coupled Receptors from a Diverse N-(Substituted)glycine Peptoid Library," J. Med. Chem. 37:2678-2685, 1994.

Patient samples

| | Fold Change | SD | onset age |
|---|---|---|---|
| NPC4 | 12.30179571 | 1.692365238 | 0.01 |
| NPC13 | 13.3 | 1.01 | 8 |
| NPC15 | 4.956993134 | 1.739496853 | 39 |
| NPC24 | 7.138343092 | 2.220336817 | 5 |
| NPC25 | 22.39 | 3.42 | 3 |
| NPC26 | 10.91171585 | 3.919829441 | 18 |
| NPC27 | 16.2325321 | 3.836615261 | 0.01 |
| NPC34 | 25.25 | 3.68 | 1.7 |
| NPC37 | 15.6 | 3.07 | 5 |
| NPC53 | 7.89 | 0.96 | 18 |
| NPC55 | 6.74 | 0.78 | 17 |

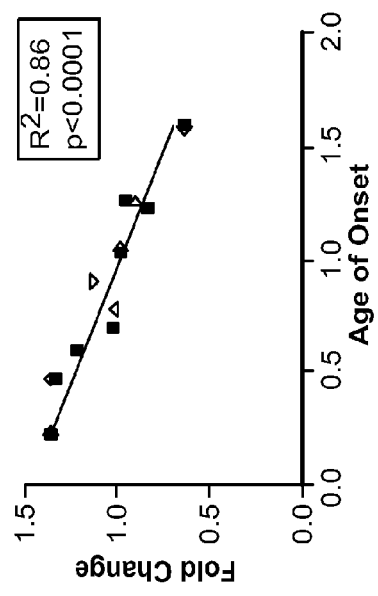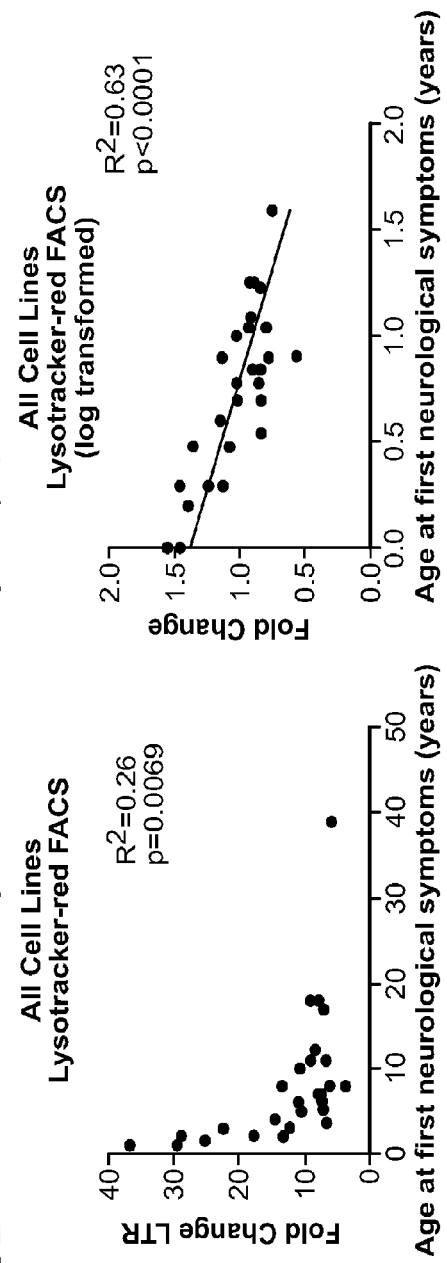
FIG. 3A
FIG. 3B

FIG. 7
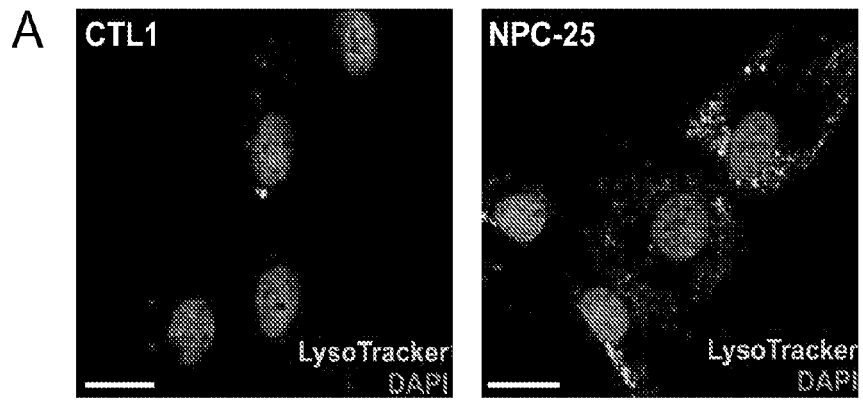
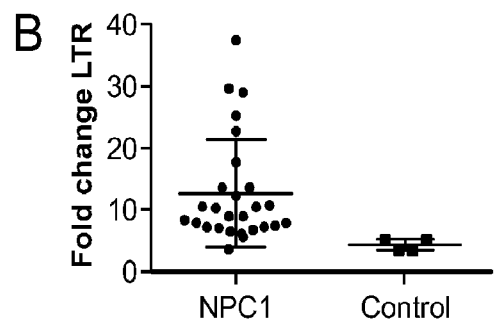
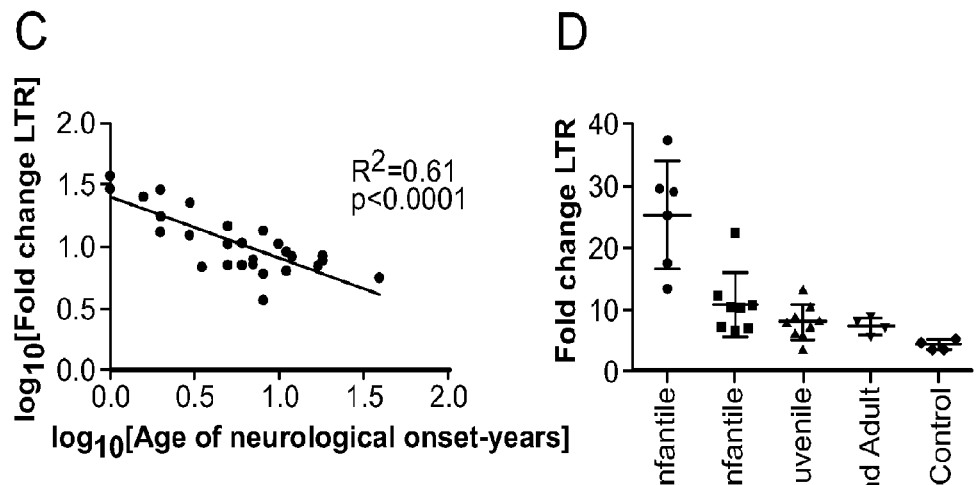

FIG. 10
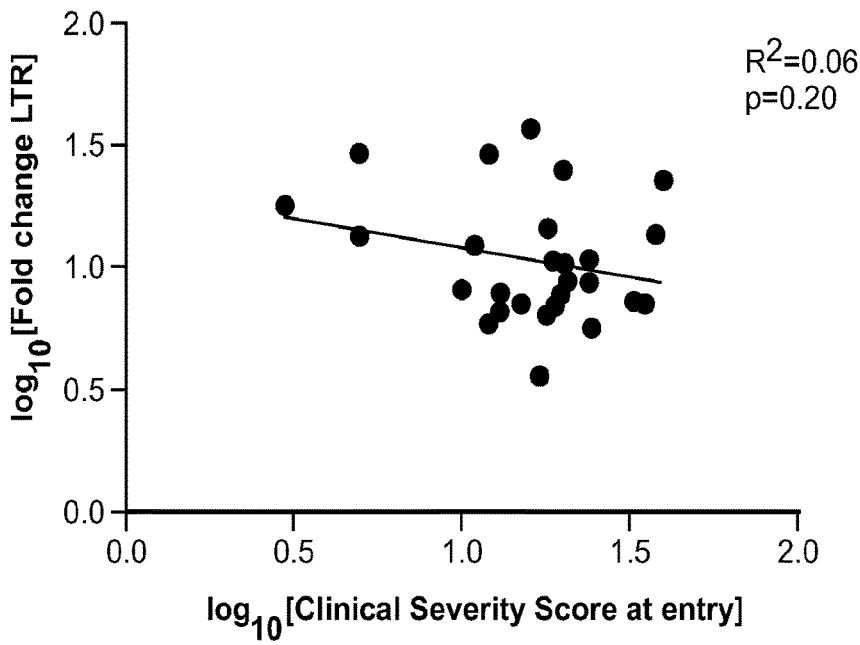
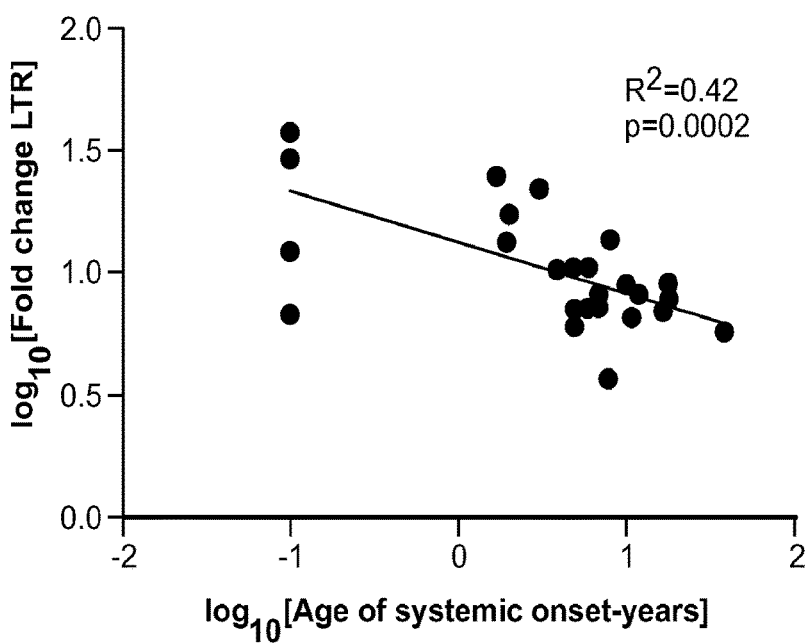

COMPOSITIONS AND METHODS FOR PREDICTING AGE OF ONSET OF A LYSOSOMAL STORAGE DISEASE OR A DISEASE ASSOCIATED WITH A LYSOSOMAL DEFECT

RELATED APPLICATIONS

This application is national stage entry of International Application No. PCT/US2014/28986, which was filed Mar. 14, 2014, and which claims priority to U.S. Provisional Application No. 61/781,807, filed on Mar. 14, 2013, the contents each of which are incorporated by reference in their entireties herein.

STATEMENT OF RIGHTS TO INVENTIONS MADE UNDER FEDERALLY SPONSORED RESEARCH

This work was supported by the National Institutes of Health. The government has certain rights in the invention.

BACKGROUND OF THE INVENTION

Advances in human genomic sequencing are revealing disease-causing mutations at younger ages, allowing improved patient management through earlier disease prediction. However in some diseases, such as the rare, recessive lysosomal storage disorder Niemann-Pick disease, type C1 (NPC1; MIM #257220), accurate prognostic information is difficult because NPC1 disease is extremely heterogeneous in the timing of clinical presentation (early infancy to adulthood), is associated with a wide spectrum of causative NPC1 (Gene ID 4864) mutations, and shows little concordance between the predicted consequences of NPC1 gene mutation on protein function with time of onset or severity of the disease [1,2].

Niemann-Pick disease (NPD) refers to a group of fatal inherited metabolic disorders that are associated with defects in the metabolism of sphingolipids. NPC1 encodes a transmembrane protein involved in intracellular cholesterol trafficking, and its mutation causes intracellular accumulation of unesterified cholesterol in late endosomal/lysosomal structures and marked accumulation of glycosphingolipids, especially in neuronal tissue. The NPC1 protein mediates intracellular cholesterol trafficking via binding of cholesterol to its N-terminal domain. Clinical signs and symptoms associated with Niemann-Pick disease, type C include defects in ambulation, cognition, eye movement, fine motor, hearing, memory, seizures, speech, and swallowing. Consequently, NPC1 disease presents with hepatosplenomegaly and neurological degeneration that leads to premature death. Current diagnosis of NPC1 involves clinical assessments as well as analysis of genetic and biochemical parameters to predict time of onset of neurological symptoms, and highlights the need for new, more informative assays for NPC1 disease. Moreover, the lifespan of subjects with NPD is related to the age of onset. At present, it is not possible to predict the age of NPD onset. Methods for predicting the age of onset are urgently required.

SUMMARY OF THE INVENTION

As described below, the present invention features diagnostic compositions and methods for predicting the age of onset of a lysosomal storage disease (e.g., NPD) and of diseases associated with lysosomal or autophagic defects (e.g., Parkinson's disease, Alzheimer's disease) in a subject.

In one aspect, the invention provides a method of predicting the age of disease onset in a subject having a lysosomal storage disease or a disease associated with a lysosomal defect, the method involving detecting fluorescence in a cell sample of the subject before and after contacting the cell with a detectable probe that accumulates in acidic cellular compartments; and calculating the fold-change in fluorescence and comparing it to a reference, wherein the fold-change in fluorescence is indicative of the age of lysosomal storage disease onset or onset of a disease associated with a lysosomal defect. In one embodiment, the lysosomal storage disease is Batten (CLN2), Fabry, Farber, Niemann-Pick disease type A, Sanfilippo type B (MPS IIIB), or Tay-Sachs diseases. In another embodiment, the disease associated with a lysosomal defect is Parkinson's disease or Alzheimer's disease.

In another aspect, the invention provides a method of predicting the age of disease onset in a subject having Niemann-Pick Disease, the method involving detecting fluorescence in a cell sample of the subject before and after contacting the cell with a detectable probe that accumulates in acidic cellular compartments; and calculating the fold-change in fluorescence and comparing it to a reference, wherein the fold-change in fluorescence is indicative of the age of Niemann-Pick Disease onset.

In another aspect, the invention provides a method for identifying an agent useful in treating a lysosomal storage disease or a disease associated with a lysosomal defect, the method involving detecting fluorescence in a cell sample of the subject before and after contacting the cell with a detectable probe that accumulates in lysosomes; calculating the fold-change in fluorescence and comparing it to the fold-change measured in a reference sample obtained from an unaffected control subject; and contacting the cell sample with a candidate agent and detecting a change in the fold-fluorescence, wherein an agent that reduces the fold-change to about the level of the fold-change present in the reference is identified as an agent useful in treating the lysosomal storage disease or disease associated with a lysosomal defect. In one embodiment, the method is used to monitor treatment or select a treatment for the subject. In another embodiment, the lysosomal storage disease is selected from the group consisting of Batten (CLN2), Fabry, Farber, Niemann-Pick disease type A, Sanfilippo type B (MPS IIIB), and Tay-Sachs diseases. In another embodiment, the disease associated with a lysosomal defect is Parkinson's disease or Alzheimer's disease.

In various embodiments of any of the above aspects or any other aspect of the invention delineated herein, the greater the fold-change in fluorescence the younger the age of disease onset and the smaller the fold-change in fluorescence the older the age of disease onset.

In one embodiment, a fold-change in flourescenece greater than 15 is indicative of a younger disease onset.

In another embodiment, the younger the age of disease onset refers to the age range from neonate to 2 years. In another embodiment, the older the age of disease onset refers to an age greater than 6 years.

In one embodiment, fluorescence is detected by a Fluorescence activated cell sorter, fluorescence spectroscopy, or microfluorimetry. In another embodiment, the detectable probe is selected from the following:

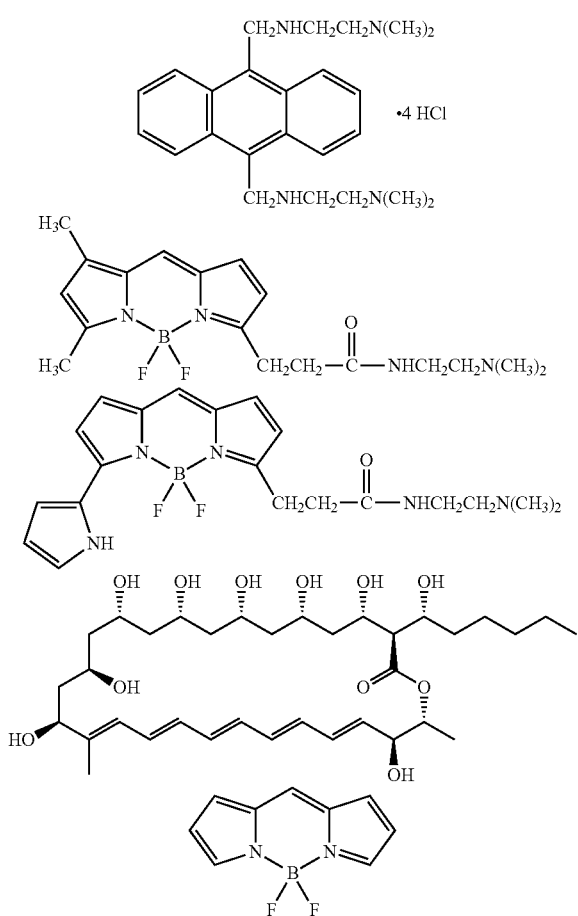

In particular embodiments of the above aspects, the cell sample contains epithelial cells, fibroblasts, or white blood cells. In other embodiments, the cell sample is obtained in a biopsy or as a blood sample. In still other embodiments, the subject is identified as having a mutation in SMPD1, NPC1 or NPC2.

Accordingly, the invention provides diagnostic compositions and methods for predicting the age of onset of a lysosomal storage disease (e.g., NPD) and of diseases associated with lysosomal or autophagic defects (e.g., Parkinson's disease, Alzheimer's disease) in a subject. Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "ameliorate" is meant to decrease, suppress, attenuate, diminish, arrest, or stabilize the development or progression of a disease.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%.

By "biologic sample" is meant any tissue, cell, fluid, or other material derived from an organism.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "detect" or "detecting" is meant identifying the presence, absence or amount of the analyte to be detected. As used herein, the term "detecting" refers to both quantitative and qualitative determinations, and as such, the term "detecting" is used interchangeably herein with "determining," "measuring," and the like.

By "disease" is meant any condition or disorder that damages or interferes with the normal function of a cell, tissue, or organ. The term "lysosomal storage disease" or "a disease associated with a lysosomal defect" is meant to refer to genetic diseases and metabolic disorders that result from defects in lysosomal function. Lysosomal storage diseases are caused by lysosomal dysfunction, usually as a consequence of deficiency of a single enzyme required for the metabolism of lipids, glycoproteins or so-called mucopolysaccharides. Like other genetic diseases, individuals inherit lysosomal storage diseases from their parents. Although each disorder results from different gene mutations that translate into a deficiency in enzyme activity, they all share a common biochemical characteristic—nearly all lysosomal disorders originate from an abnormal accumulation of substances inside the lysosome.

Examples of diseases include, but are not limited to, Niemann-Pick disease and other lysosomal storage diseases. Lysosomal storage diseases include Batten (CLN2), Fabry, Farber, Niemann-Pick disease type A, Sanfilippo type B (MPS IIIB), Wolman disease, and Tay-Sachs diseases.

By "marker" is meant any protein, polynucleotide, or cellular metabolite having an alteration in level or activity that is associated with a disease or disorder.

By "marker profile" is meant a characterization of the expression or expression level of two or more markers.

As used herein, "obtaining" as in "obtaining an agent" includes synthesizing, purchasing, or otherwise acquiring the agent.

By "periodic" is meant at regular intervals. Periodic patient monitoring includes, for example, a schedule of tests that are administered daily, bi-weekly, bi-monthly, monthly, bi-annually, or annually.

By "reduces" is meant a negative alteration of at least 10%, 25%, 50%, 75%, or 100%.

By "reference" is meant a standard for comparison or control condition. In one embodiment, a reference is a standard curve.

By "subject" is meant to include, but is not limited to, a mammal, including, but not limited to, a human or a non-human mammal, such as a non-human primate, murine, bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A shows a FACS analysis of patient sample NPC4. Fluorescence values for stained (blue), unstained (Red), and corrected by Cyclodextrin treatment (yellow and green) cell samples are shown in NPC4 cells. FIG. 1B shows an analysis of fold-change fluorescence in 30 NPC subjects that range in age from infants to adults.

FIGS. 3A-3C show an analysis of Lysotracker staining in subjects with NPC. FIG. 3A is a graph showing that fold change in fluorescence correlates with subject age at the time of disease onset. FIG. 3B is a graph showing that age of onset of neurological symptoms correlates with fold-change in fluorescence. FIG. 3C shows that age of onset of neurological symptoms correlates with fold-change in fluorescence. In subjects with early infantile NPC there is a 20-35 fold change in fluorescence. A 5-15 fold change is seen in older subjects.

FIG. 7(A-D) shows fibroblasts from individuals with NPC1 show quantitative increases in lysosomal storage defects that correlate with age of onset of neurological symptoms. (A) Confocal microscopic images of LysoTracker Red staining in fibroblasts from an individual with NPC1 (NPC-25, right) compared to control fibroblasts (CTL1, left). Increased cellular staining in NPC1 is consistent with increased cholesterol storage in late endosomes/lysosomes. Nuclear DAPI staining in blue; scale bar=20 µm. (B) Scatter dot plot comparing LysoTracker staining (LTR; y-axis) of individual, NPC1 patient-derived fibroblast lines (N=27) with staining of control fibroblast lines (N=4). NPC1 fibroblasts exhibit significantly greater LysoTracker staining than control cells (Student's two-tailed t-test, $p<0.0001$) with greater variance (NPC1 standard deviation=8.6, Control standard deviation=4.4). (C) Linear regression of fold change increases in LysoTracker staining intensity of NPC1 cells (y-axis) versus the age of onset of neurological symptoms (x-axis) showed significant correlation. Each blue circle represents results from a single NPC1 patient cell line. Log 10-transformed values are presented and were used for statistical analyses of these normally distributed data. (D) Scatter dot plot of NPC1 patients sorted into categories based upon neurological age of onset, as follows: early infantile (2 months-2 years), n=6; late infantile (2-6 years), n=8; juvenile (6-15 years), n=9; and adolescent/adulthood (≥15 years), n=4. LysoTracker staining intensity for early infantile was significantly different from that of all other categories (1-way ANOVA with Tukey's post-hoc test; $p<0.0001$). For (B-D), LysoTracker staining measurements are expressed as fold increase over unstained cells derived from the same individual, to remove any effects of autofluorescence. Box and whiskers plots in (B, D) show mean and standard deviation. Statistical analyses performed using Prism (GraphPad).

FIGS. 10 (A and B) shows fibroblasts from individuals with NPC1 disease show quantitative increases in lysosomal storage defects that correlate strongly with age of onset of systemic symptoms. (A-B) Linear regression of fold change increases in LysoTracker staining intensity of NPC cells (y-axis) versus A) the Clinical Severity Score at entry into the Natural History study, and B) the age of onset of any systemic symptoms (each on respective x-axes). Each blue circle represents results from a single individual. Significant correlation was present for systemic age of onset (B) but not clinical severity score (A). $Log_{10}$-transformed values are presented and were used for statistical analyses of these normally distributed data. Statistical analyses performed using Prism (GraphPad).

DETAILED DESCRIPTION OF THE INVENTION

Figure 1A:
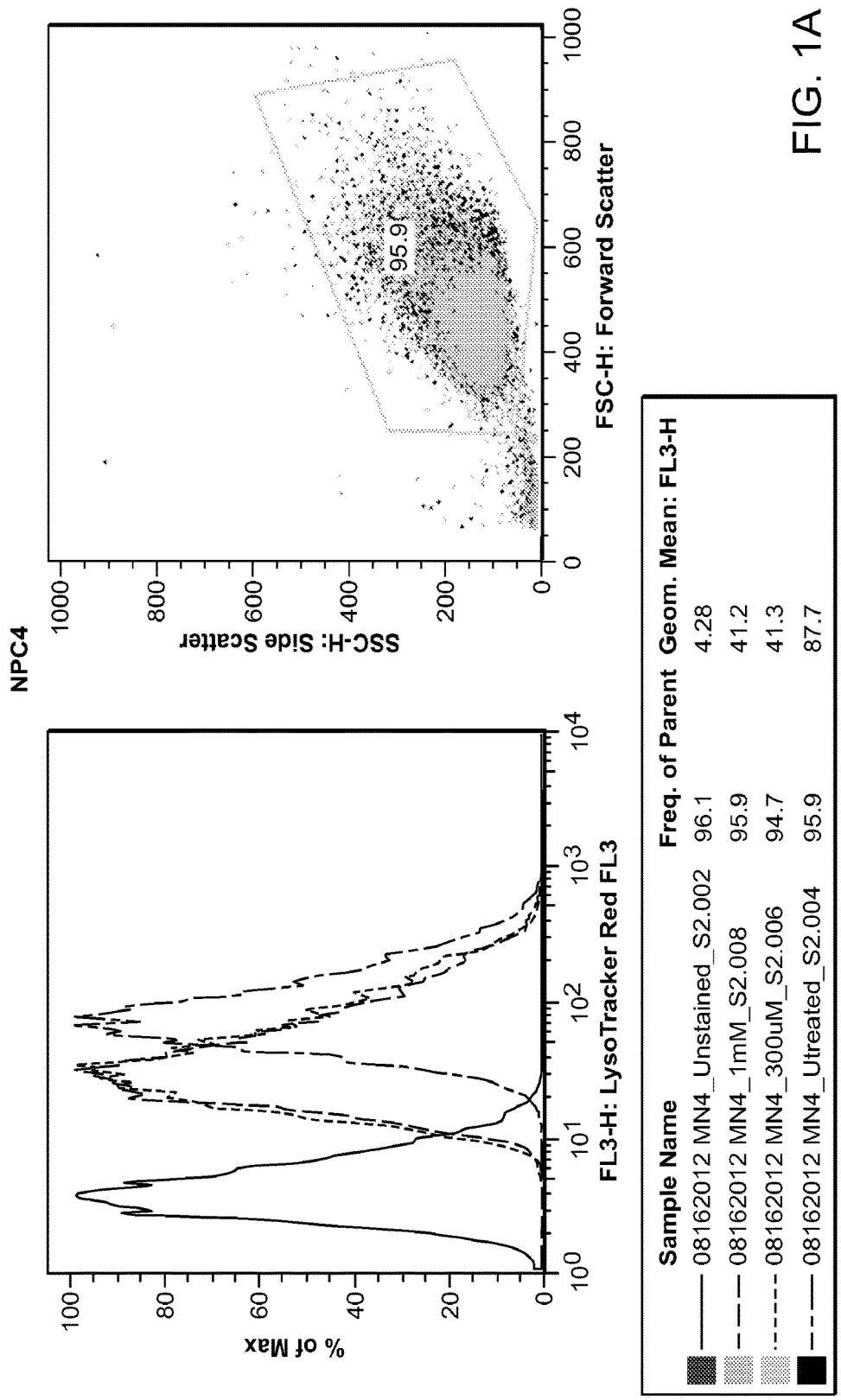
FIGS. 1A and 1B show an analysis of Lysotracker staining in subjects with NPC.

The invention features compositions and methods that are useful for predicting the age of onset of a lysosomal storage disease (e.g., NPD, NPD type C1) and of diseases associated with lysosomal or autophagic defects (e.g., Parkinson's disease, Alzheimer's disease) in a subject, and for identifying agents useful in ameliorating NPD symptoms.

The invention is based, at least in part, on the discovery that fold-change in lysosomal fluorescence (stained vs. unstained) in cells (e.g., fibroblasts) of a subject identified as having a genetic change associated with NPD correlates with age of NPD onset in the subject.
Diagnostics The present invention features methods for predicting the age of onset of a lysosomal storage disease (e.g., NPD, type C1) and of diseases associated with lysosomal or autophagic defects (e.g., Parkinson's disease, Alzheimer's disease) in a subject.
Lysosomal Storage Diseases Lysosomal storage diseases, also referred to herein as lysosomal storage disorders or LSDs, are a group of rare inherited metabolic disorders that result from defects in lysosomal function. LSDs result when a specific organelle in the body's cells—the lysosome—malfunctions. LSDs are caused by lysosomal dysfunction usually as a consequence of deficiency of a single enzyme required for the metabolism of lipids, glycoproteins or so-called mucopolysaccharides. Individually, LSDs occur with frequencies of about 1:10,000 to 1:250,000, however, as a group the incidence is about 1:5,000. Most of these disorders are autosomal recessively inherited; however, a few are X-linked inherited, such as Fabry disease and Hunter syndrome (MPS II).

Like in other genetic diseases, individuals typically inherit lysosomal storage diseases from their parents. Although each disorder results from different gene mutations that translate into a deficiency in enzyme activity, they all share a common biochemical characteristic—nearly all lysosomal disorders originate from an abnormal accumulation of substances inside the lysosome. Lysosomal storage diseases affect mostly children and they often die at a young and unpredictable age, many within a few months or years of birth.

The symptoms of lysosomal storage disease vary, depending on the particular disorder and other variables like the age of onset, and can be mild to severe. They can include developmental delay, movement disorders, seizures, dementia, deafness and/or blindness. Some people with lysosomal storage disease have enlarged livers (hepatomegaly) and enlarged spleens (splenomegaly), pulmonary and cardiac problems, and bones that develop abnormally.

There are no causative cures for lysosomal storage diseases and treatment is mostly symptomatic. Niemann-Pick disease is a disease of a subgroup of LSDs, called sphingolipidoses or lipid storage disorders in which harmful quantities of fatty substances, or lipids, accumulate in the spleen, liver, lungs, bone marrow, and brain.

Niemann-Pick disease is inherited in an autosomal recessive pattern, which means both copies, or alleles, of the gene must be mutated (altered in such a way that function is impaired, in contrast to a polymorphism, in which the nucleotide sequence is altered but causes no functional disruption) for a person to be affected by the disorder. Most often, the parents of a child with an autosomal recessive disorder are not affected but are carriers of one copy of the altered gene. NPD can be classified as follows:

Niemann-Pick disease, SMPD1-associated, which includes types A and B; and

Niemann-Pick disease, type C, which includes types C1 and C2 and Niemann-Pick disease, type D, which is caused by the same gene as type C1.

Mutations in the SMPD1 gene cause Niemann-Pick disease types A and B, and mutations in NPC1 and NPC2 cause Niemann-Pick disease, type C, which is also referred to herein as NPC.

Type D was originally separated from Type C to delineate a group of patients with otherwise identical disorders who shared a common Nova Scotian ancestry. Patients in this group are now known to share a specific mutation in the NPC1 gene, and NPC is now used to embrace both groups.

In the classic infantile type A variant, a missense mutation causes complete deficiency of sphingomyelinase. Sphingomyelin is a component of cell membrane including the organellar membrane and so the enzyme deficiency blocks degradation of lipid, resulting in the accumulation of sphingomyelin within lysosomes in the macrophage-monocyte phagocyte lineage. Affected cells become enlarged, sometimes up to 90 micrometers in diameter, secondary to the distention of lysosomes with sphingomyelin and cholesterol. Histology demonstrates lipid laden macrophages in the marrow, as well as "sea-blue histiocytes" on pathology. Numerous small vacuoles of relatively uniform size are created, imparting a foamy appearance to the cytoplasm. Niemann-Pick type C is a lysosomal storage disease associated with mutations in NPC1 and NPC2 genes. Niemann-Pick Type C strikes an estimated 1:150,000 people. Approximately 50% of cases present before 10 years of age, but manifestations may first be recognized as late as the sixth decade.

The present methods for predicting the age of onset of a lysosomal storage disease and of diseases associated with lysosomal or autophagic defects can be carried out in subjects that include those with a genetic mutation associated with NPD and are not yet exhibiting NPD symptoms.

Individuals affected by NPC may show symptoms comprising splenomegaly, hepatomegaly or hepatosplenomegaly, but this finding may be absent in later onset cases. Prolonged jaundice or elevated bilirubin can present at birth. In some cases, however, enlargement of the spleen and/or liver does not occur for months or years—or not at all. Enlargement of the spleen and/or liver frequently becomes less apparent with time, in contrast to the progression of other LSD such as NPA and NPB or Gaucher's disease. Organ enlargement does not usually cause major complications.

Progressive neurological disease is the hallmark of NPC and is responsible for disability and premature death in all cases beyond early childhood. Children with NPC may initially present with delays in reaching normal developmental milestones skills before manifesting cognitive decline, i.e. dementia for example.

Neurological signs and symptoms include cerebellar ataxia, dysarthria, dysphagia, tremor, both partial and generalized epilepsy, vertical supranuclear palsy comprising upgaze palsy, downgaze palsy, saccadic palsy or paralysis, sleep inversion, gelastic cataplexy, dystonia, most commonly begins with in turning of one foot when walking (action dystonia) and may spread to become generalized, spasticity, hypotonia, ptosis, microcephaly, psychosis, progressive dementia, progressive hearing loss, bipolar disorder, major and psychotic depression that can include hallucinations, delusions, mutism, or stupor. In the terminal stages of NPC, the patient is bedridden, with complete ophthalmoplegia, loss of volitional movement and has severe dementia.

A subject is considered to be a healthy subject with regard to Niemann-Pick disease, if the subject does not suffer from symptoms associated with Niemann-Pick disease. Moreover in an embodiment of the methods of the invention a subject will be considered to be healthy regarding Niemann-Pick disease type C, if it has no mutation of the functional parts of the NPC1 and NPC2 genes and/or no mutation of the NPC1 and NPC2 genes resulting in a reduction of or deficiency of the respective proteins or the activity thereof, resulting in symptoms associated with Niemann-Pick disease type C. The methods of the present invention are also suitable for a Niemann-Pick disease type C carrier.

In one embodiment of the present invention, the methods involve obtaining a biological sample from the subject, and isolating cells from that sample for in vitro culture. In another embodiment, cells obtained as a biological sample are not cultured, but are gently homogenized to yield a whole cell suspension, which can be used in the methods of the invention. The fluorescence of the living cells is detected before and after the cells are contacted with a detectable probe that accumulates selectively in lysosomes (e.g., Lysotracker). The fold-change in fluorescence intensity before and after contact with the dye correlates with age of disease onset. In general, the fold-change in fluorescence intensity is greatest in young children, whereas adults who have the genetic mutation lave a lesser increase in fold-change of fluorescence intensity.

The diagnostic methods described herein can be used individually or in combination with any other diagnostic method known in the art for a more accurate prediction of age of NPD onset. For example, Lysotracker staining is carried out before, following or concurrently with genetic analysis of a mutation associated with NPD.

Monitoring

The disease state or treatment of a subject having NPC can be monitored using the methods of the invention. In embodiments, methods of the invention are used by a clinician to identify subjects as having or not having NPC. For example, a general practitioner may use the methods delineated herein to screen patients for the presence of NPC. In embodiments, detecting fluorescence in a cell sample of a subject before and after contacting the cell with a detectable probe that accumulates in acidic cellular compartments is monitored. Such monitoring may be useful, for example, in assessing the efficacy of a particular drug in a subject or in assessing disease progression.

In some embodiments, fold-change in fluorescence is monitored prior to administering therapy. These results provide a baseline that describes the level of the biomarker(s) prior to treatment.

Accordingly, methods of the invention are also useful in monitoring treatment efficacy in an NPD subject. In some embodiments, fold-change in fluorescence is monitored periodically. In other embodiments, fold-change in fluorescence is monitored periodically throughout treatment. Agents shown to be useful in normalizing fold-change in fluorescence include Tocopherol, cyclodextrin, and HDAC inhibitors. To monitor the treatment of a subject with NPD, cells are obtained from that subject periodically before and during treatment. The cell samples are then analyzed to determine fold-change in fluorescence at various time points. Agents that reduce fold-change in fluorescence of cells obtained from patients treated with the agent relative to the fold-change in fluorescence of cells prior to treatment are identified as effective for the treatment of NPD.

In certain embodiments, a fold-change in fluorescence greater than 15 is indicative of a younger disease onset.

Treatment Selection

Methods of the invention are not only useful for predicting the age of onset of a lysosomal storage disease (e.g., NPD) and of diseases associated with lysosomal or autophagic defects (e.g., Parkinson's disease, Alzheimer's disease) in a subject, but are also useful in treatment selection methods.

Accordingly, in the methods of the invention for predicting the age of disease onset in a subject having a lysosomal storage disease or a disease associated with a lysosomal defect, the person skilled in the art may recommend to apply, maintain, reduce, elevate or not apply a therapy or to perform further diagnostic tests.

It is thus an embodiment of the method of the present invention for predicting the age of disease onset in a subject having a lysosomal storage disease or a disease associated with a lysosomal defect that the method comprises giving a recommendation whether a therapy should be applied, maintained, reduced, elevated or not applied.

For example, as shown in detail below, cyclodextrin can be used on cells in vitro to normalize the fold-change in fluorescence observed in cells of NPD subjects. Agents shown to be useful in normalizing fold-change in fluorescence include Tocopherol, cyclodextrin, and HDAC inhibitors. To identify an agent useful for the treatment of a subject with NPD, cells are obtained from that subject, and analyzed to determine fold-change in fluorescence in cells contacted with the agent and in uncontacted cells. Agents that normalize fold-change in fluorescence relative to the fluorescence of untreated cells are identified as useful for the treatment of NPD in the subject from whom the cell sample was obtained.

Types of Biological Samples

The level of lysosomal staining is measured in different types of biologic samples. In one embodiment, the biologic sample comprises cells derived from a subject diagnosed as having NPD and cultured in vitro. While any somatic cell may be used, fibroblasts that are obtained during a skin biopsy and white blood cells present in blood samples are particularly convenient.

Detectable Probes

The invention provides methods for predicting the age of NPD onset that involve detecting the fluorescence of a cell derived from a subject having NPD before and after the cell is contacted with a detectable probe that accumulates in lysosomes. In one embodiment, the detectable probe is a weakly basic amine that selectively accumulates in cellular compartments with low internal pH (e.g., lysosomes, autophagosomes). Fluorescent acidotropic probes useful in the methods of the invention include the commercially available LysoTracker® probes, as well as Fillipin, and boron-dipyrromethene (Bodipy). The intensity of lysosomal fluorescence is an indication of lysosome size. Thus, fluorescence intensity can be used interchangeably with fold-change in fluorescence. Probes useful in the methods of the invention preferably selectively label acidic organelles at nanomolar concentrations.

The LYSOTRACKER probes comprise a fluorophore linked to a weak base that is only partially protonated at neutral pH, are freely permeant to cell membranes and typically concentrate in spherical organelles. In LysoTracker® dye-stained cells, the lysosomal fluorescence may constitute only a small portion of total cellular fluorescence. Typically, such fluorescence is detected and/or quantitated by flow cytometry or fluorometry. Lysotracker probes include the following:

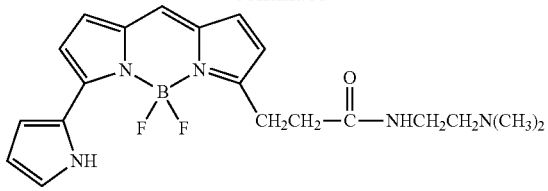

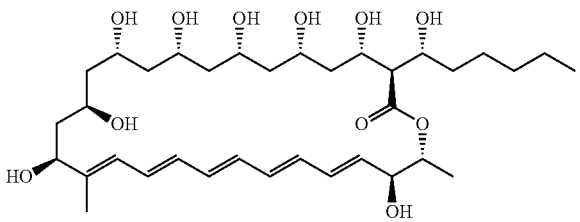 [SMILES: CCCCC[C@@H](O)[C@H]1C(=O)O[C@H](C)[C@@H](O)/C=C/C=C/C=C/C=C/C=C(\C)[C@@H](O)C[C@H](O)C[C@H](O)C[C@H](O)C[C@H](O)C[C@H](O)C[C@@H]1O]

The structure of fillipin follows:

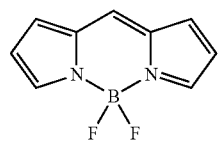

The structure of bodipy follows:

Detectable probes useful in the methods of the invention and methods for using and making them are known in the art and described, for example, in Cell 52, 329 (1988); Lysosomes in Biology and Pathology, J. T. Dingle et al., Eds., North-Holland Publications Co. (1969); 3. J Cell Biol 106, 539 (1988); Cytometry suppl 7, 77 abstract #426B (1994); Mol Biol Cell 5, 113a abstract #653 (1994); J Cell Biol 126, 877 (1994); J Cell Biol 128, 901 (1994); Molecular Aspects of Anticancer Drug Action, S. Neidle and M. J. Waring, Eds., Macmillian (1983) pp. 233-282; J Biol Chem 265, 4775 (1990); and Nature 352, 70 (1991), each of which is incorporated by reference in their entireties.

Kits

The invention further provides kits for diagnosing NPD. In one embodiment, the kit includes a detectable probe that accumulates in lysosomes (e.g., Lysotracker) and directions for correlating staining intensity with age-of-onset. In some embodiments, the kit comprises a sterile container which contains the binding agent; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments. The instructions will generally include information about the use of the composition for correlating lysosomal staining with age of NPD onset. In other embodiments, the instructions include at least one of the following: warnings; indications; counter-indications; animal study data; clinical study data; and/or references. The instructions may be printed directly on the container (when present), or as a label applied to the container, or as a separate sheet, pamphlet, card, or folder supplied in or with the container.

Screening Assays

The invention provides methods for identifying therapeutic agents useful for the treatment of Niemann-Pick disease.

Such agents are identified by assaying for a reduction in fold-change of lysosomal staining. The utility of the present methods for identifying agents useful in treating NPD is shown in the results reported herein below for methyl cyclodextrin.

Cyclodextrins form stable aqueous complexes with many other chemicals. More recently, cyclodextrin was shown to move cholesterol out of lysosomes in Niemann Pick Type C disease. NPD is a lysosomal storage disease causing progressive deterioration of the nervous system and dementia. It usually affects young children by interfering with their ability to metabolize cholesterol at the cellular level. Numerous research studies have followed showing that Hydroxypropyl Beta Cyclodextrin (HPβCD) and methyl cyclodextrin are not simply agents that solubilize drugs, but they have powerful pharmacological properties. In particular, both (β-cyclodextrin and Methyl-β-cyclodextrin (MβCD) remove cholesterol from cultured cells. The methylated form MβCD was found to be more efficient than β-cyclodextrin. As reported herein, the activity of cyclodextrin, and agents with similar activities, can be detected using methods of the present invention.

Accordingly, methods of the invention are useful for the high-throughput low-cost screening of candidate agents for the treatment of Niemann-Pick disease. A candidate agent that reduces the fold-change in fluorescence intensity in NPD cells is then isolated and tested for activity in an in vivo assay for its ability to ameliorate the symptoms of NPD or other lysosomal storage diseases. In one embodiment, the high-throughput screening involves screening arrays comprising siRNAs. One skilled in the art appreciates that the effects of a candidate agent on a cell is typically compared to a corresponding control cell not contacted with the candidate agent. Thus, the screening methods include comparing the fluorescence intensity in NPD cells contacted by a candidate agent to the fluorescence intensity of an untreated control cell.

Agents isolated by this approach may be used, for example, as therapeutics to treat or prevent the onset of NPD disease or a lysosomal storage disease.

Test Compounds and Extracts

In general, agents that reduce the fold-change in fluorescence intensity in NPD cells are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., Proc. Natl. Acad. Sci. U.S.A. 90:6909, 1993; Erb et al., Proc. Natl. Acad. Sci. USA 91:11422, 1994; Zuckermann et al., J. Med. Chem. 37:2678, 1994; Cho et al., Science 261:1303, 1993; Carrell et al., Angew. Chem. Int. Ed. Engl. 33:2059, 1994; Carell et al., Angew. Chem. Int. Ed. Engl. 33:2061, 1994; and Gallop et al., J. Med. Chem. 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, Biotechniques 13:412-421, 1992), or on beads (Lam, Nature 354:82-84, 1991), chips (Fodor, Nature 364:555-556, 1993), bacteria (Ladner, U.S. Pat. No. 5,223,409), spores (Ladner U.S. Pat. No. 5,223,409), plasmids (Cull et al., Proc Natl Acad Sci USA 89:1865-1869, 1992) or on phage (Scott and Smith, Science 249:386-390, 1990; Devlin, Science 249:404-406, 1990; Cwirla et al. Proc. Natl. Acad. Sci. 87:6378-6382, 1990; Felici, J. Mol. Biol. 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to reduce the fold-change in fluorescence intensity in NPD cells further fractionation of the positive lead extract is necessary to isolate molecular constituents responsible for the observed effect. Thus, the goal of the extraction, fractionation, and purification process is the careful characterization and identification of a chemical entity within the crude extract that reduces cholesterol accumulation in lysosomes. Methods of fractionation and purification of such heterogenous extracts are known in the art. If desired, compounds shown to be useful as therapeutics are chemically modified according to methods known in the art.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Somatic Cell Defect is Associated with the Onset of Neurological Symptoms in a Lysosomal Storage Disease Example 1

Fibroblast cells obtained from patients in skin biopsies were expanded in vitro. Fluorescence levels of cell samples were quantitated by FACS analysis (FIG. 1A) before and after staining with a compound having molecular formula: $C_{20}H_{24}BF_2N_5O$ (LYSOTRACKER RED; Invitrogen) and having the following structure:

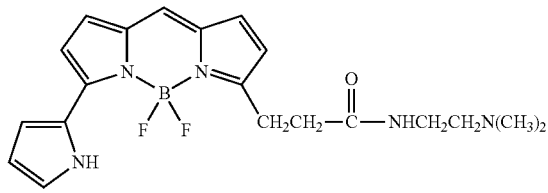

Cells were cultured in DMEM with fetal bovine serum, L-glutamine, and antibiotics at 5% $CO_2$ in a 37° C. incubator.
Cell staining was carried out as follows:
Lysotracker-Red Staining Protocol:
  Day1—Change media 24 hours before FACS analysis, if treating cells with methyl beta cyclodextrin add the drug as well.
  Day2—Note: WORK IN THE DARK, (PROTECT TUBES FROM THE LIGHT while using lysotracker-red)
    Dilute LYSOTRACKER-red (1:1000) for a final concentration of 1 µM with culture media.
    Incubate cells with lysotracker in the incubator (37° C.) for 30 minutes.
    Aspirate media and wash twice with 1×PBS (2 mls each time).
    Add 300 µls of Trypsin
    Resuspend cells into 5 mls of media and centrifuge at 1000 rpm for 10 minutes in order to obtain pellet.
    Resuspend the pellet into 500 uls of media and transfer to FACS vials at 4° C. in the dark.
    Perform FACS analysis.

Figures 1B, 2:
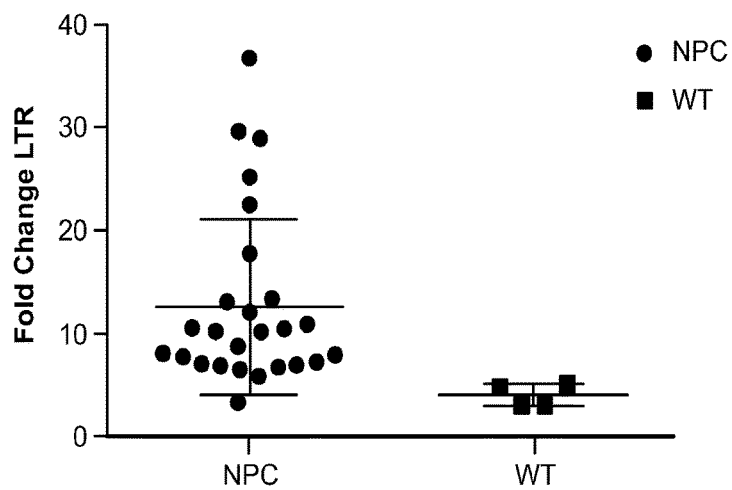
FIG. 2 is a table showing patient sample number, fold change in fluorescence and age of onset.

The fluorescence of the cell samples was quantified before and after staining and the fold change in fluorescence was calculated as the ratio of fluorescent intensity after dye/cell autofluorescence. This change was then plotted as a function of time. As shown in FIG. 1B, there is a wide range in the distribution of fold-change in NPD subjects of varying ages. Interestingly, the fold-change in fluorescence correlates with and can be used to predict age of disease onset (FIGS. 2 and 3A).

Figure 3C:
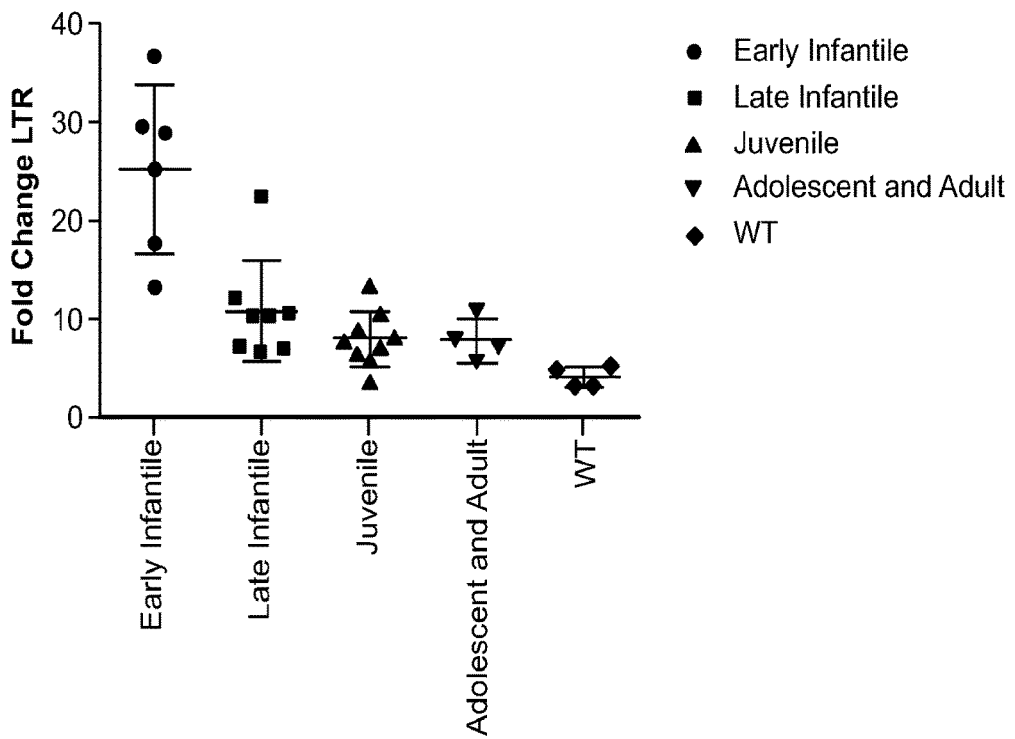

In fact, fold change in fluorescence correlates with the age of onset of neurological symptoms (FIGS. 3B and 3C). In subjects with early infantile NPC there is a 20-35 fold change in fluorescence (FIG. 3C). A 5-15 fold change is seen in older subjects (FIG. 3C).

Figure 4:
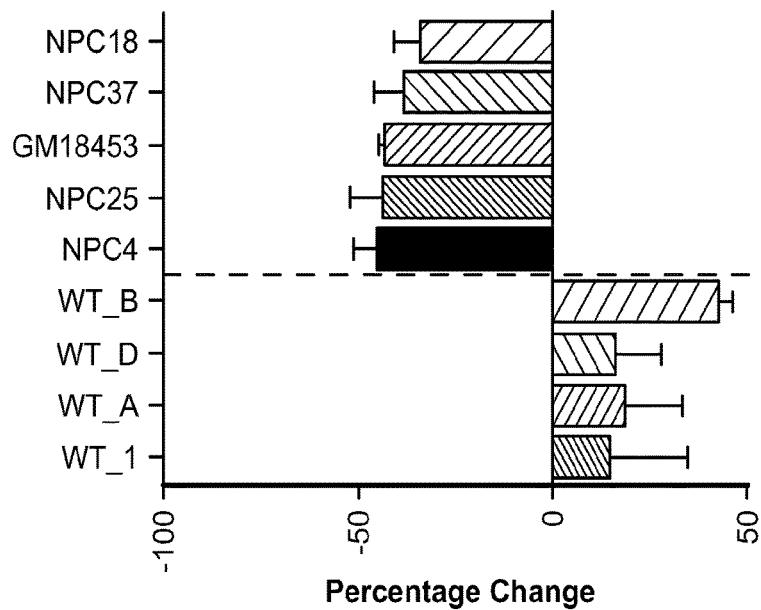
FIG. 4 is a graph showing the percentage change in fluorescence following treatment with methyl cyclodextrin in wild type and NPD patient samples.
Figure 5A:
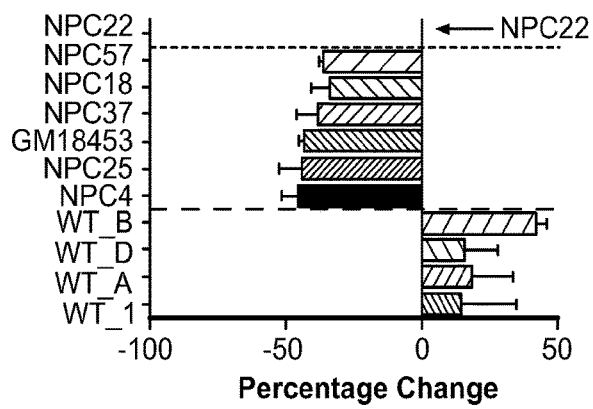
FIG. 5A is a summary graph showing the percentage change in fluorescence following treatment with methyl cyclodextrin in wild type and NPD patient samples. This graph represents results with all the cell lines treated with cyclodextrin. Results represent the average obtained in 3 experiments.
Figure 5B:
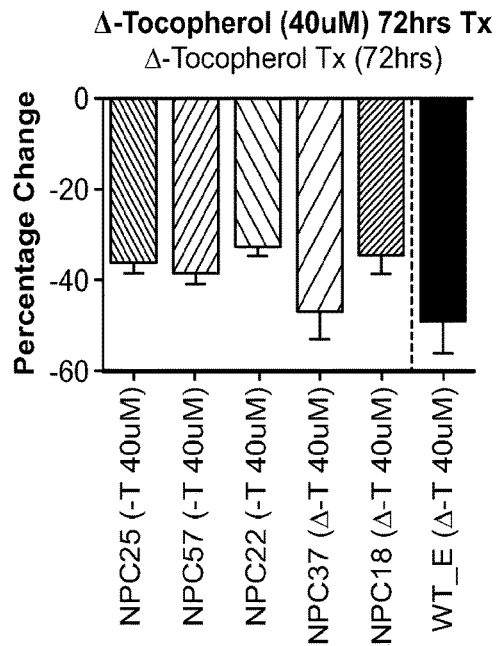
FIG. 5B shows results obtained when Tocopherol was used.

The fold change in fluorescence is reduced following treatment with methyl cyclodextrin in wild type and NPD patient samples (FIGS. 4 and 5A). Tocopherol was also effective in reducing the fold change in fluorescence.

Figure 6:
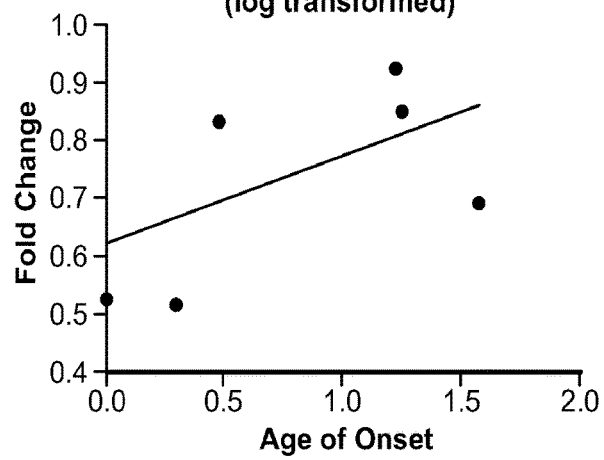
FIG. 6 shows that fold change in fluorescence does not correlate with age of disease onset in wild type subject samples.

FIG. 6 shows that fold change in fluorescence does not correlate with age of disease onset in wild type subject samples.

Example 2

Figure 8:
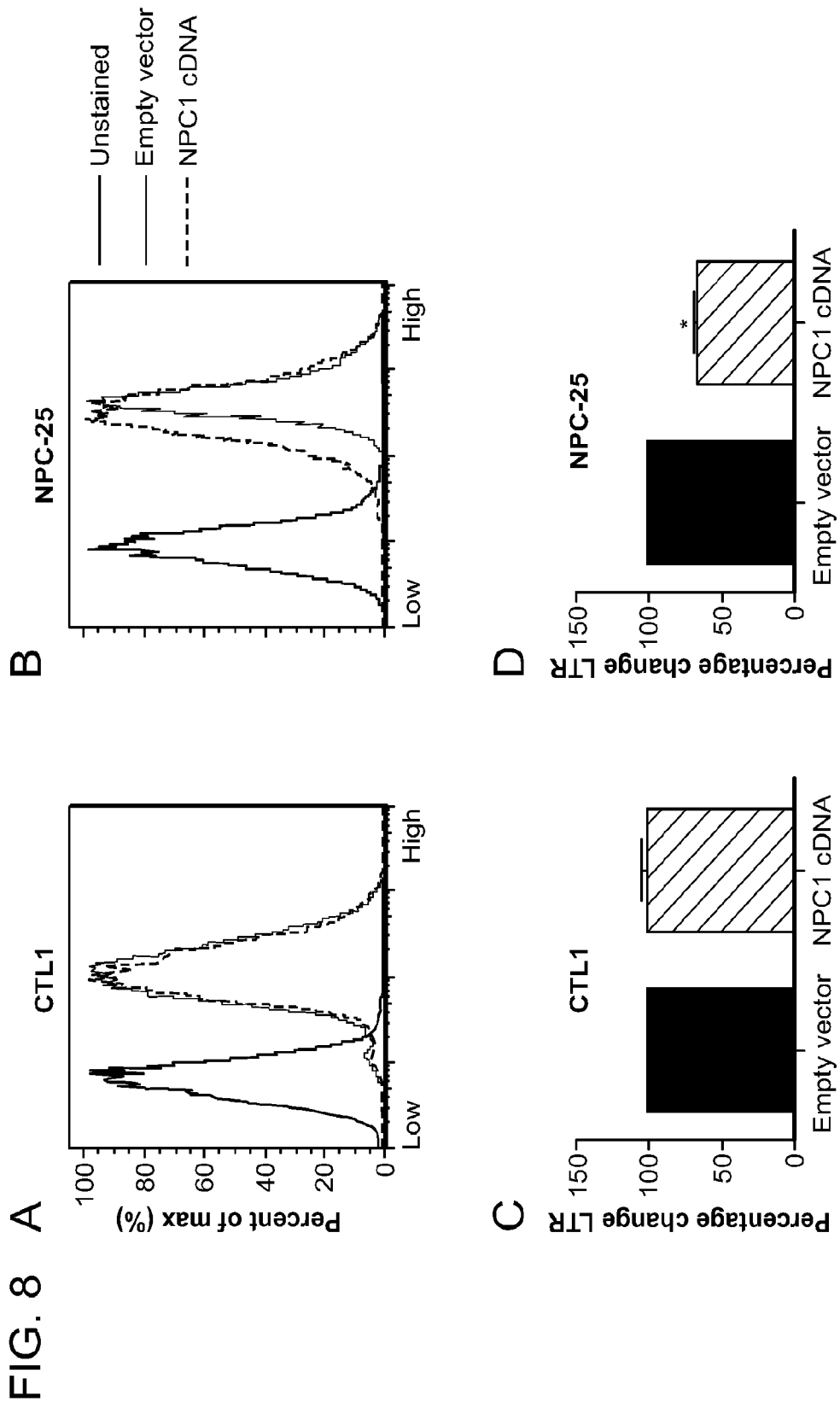
FIG. 8(A-D) shows Suppression of LysoTracker staining defect in NPC1 cells by genetic rescue with overexpression of NPC1. (A, B) Histograms of FACS analysis of control fibroblasts (A, CTL1) and fibroblasts isolated from an individual with NPC1 disease (B, NPC-25). The x-axis shows intensity of LysoTracker staining per cell from low (left) to high intensity (right), and the y-axis shows percentage of cells exhibiting a given intensity. Pink line indicates distribution of unstained cells; blue line indicates LysoTracker-stained cells transfected with an empty control vector (pLenti6.2 Vector/V5 DEST, Invitrogen); green line indicates LysoTracker-stained cells transfected with a human NPC1 cDNA expression vector (Origene, Rockville, Md.; cat. #SC120010). At 72 hours post-transfection, cells were stained with LysoTracker Red dye and analyzed by FACS. (C, D) Bar graphs comparing the percentage change of LysoTracker staining intensity (y-axis) when transfected with either empty vector (blue bar, set to 100%) or NPC1 expression vector (green bar) in control fibroblasts (C, CTL1) and fibroblasts isolated from an individual with NPC disease (D, NPC-25). Overexpression of NPC1 cDNA did not reduce LysoTracker Red staining in CTL1 fibroblasts, while staining was significantly reduced in NPC1 patient-derived fibroblasts, consistent with reduced lysosomal cholesterol content. *indicates $p=0.0009$ (Student's t-test); error bars=standard deviation. Fibroblasts were transfected using the Amaxa nucleofection protocol for normal human dermal fibroblasts (Amaxa, Gaithersburg, Md.) using nucleofection reagents (Lonza, Basel, Switzerland; cat. #CC-2511). Statistical analyses performed using Prism (GraphPad).
Figure 9:
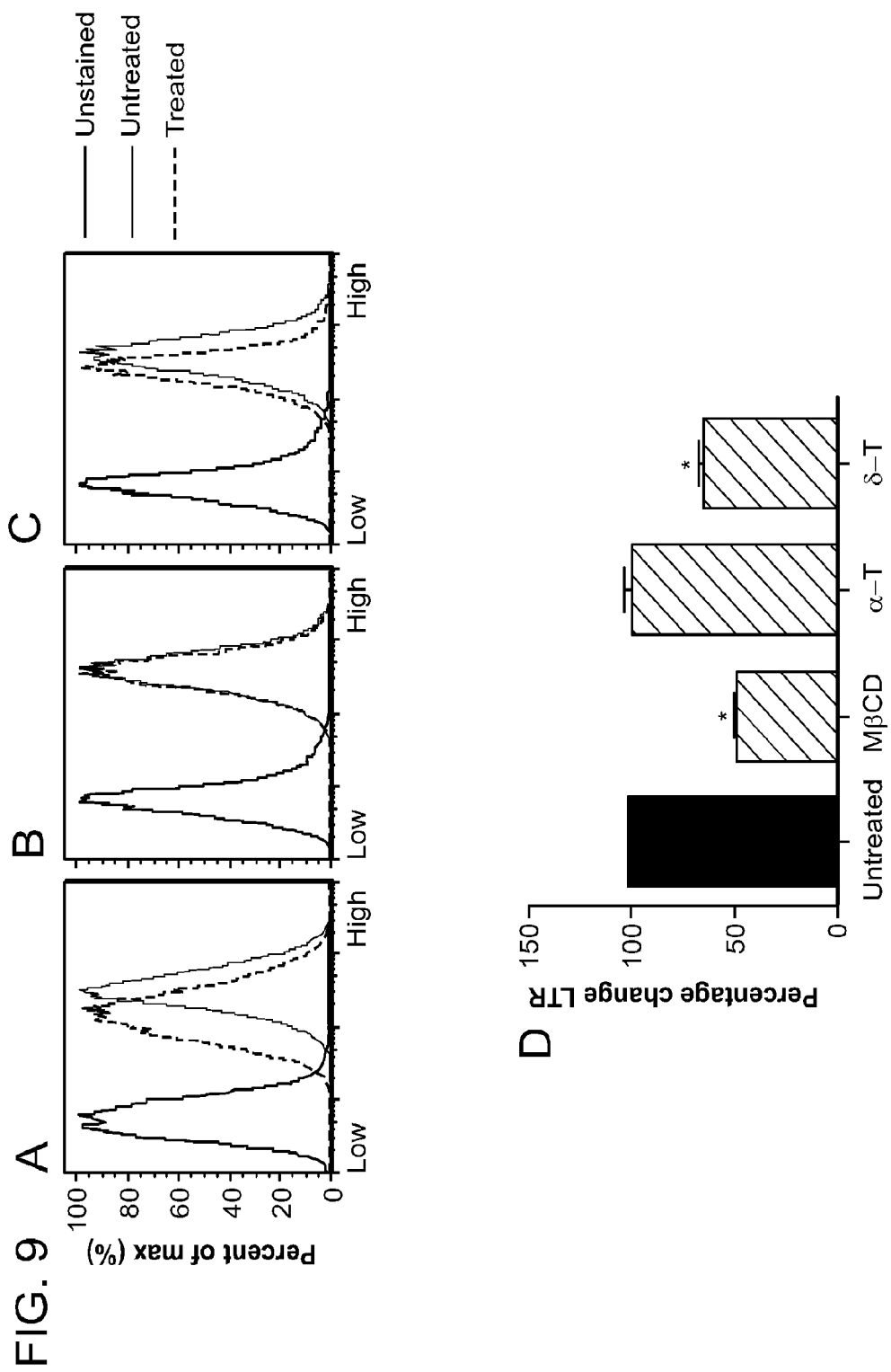
FIG. 9(A-D) shows suppression of LysoTracker staining defect in NPC1 cells by treatment with compounds previously assessed in correcting NPC1 cellular defects. (A-C) Histograms of FACS analysis of fibroblasts isolated from an individual with NPC1 disease (NPC-25) treated with (A) Methyl-β-Cyclodextrin (M(βCD), (B) α-tocopherol (α-T) or (C) δ-tocopherol (δ-T). The x-axis shows intensity of LysoTracker staining per cell from low (left) to high intensity (right), and the y-axis shows percentage of cells exhibiting a given intensity. Pink line indicates distribution of unstained cells; blue line indicates LysoTracker-stained untreated cells; green line indicates LysoTracker-stained NPC fibroblasts that had previously been treated with (A) 300 µM MβCD for 24 hours, (B) 40 µM α-T for 72 hours, or (C) 40 µM δ-T for 72 hours. (D) Bar graphs showing the percentage change of LysoTracker (y-axis) staining intensity in untreated NPC-25 cells (blue bar, set to 100%) as compared to NPC25 cells treated with MβCD, α-T or δ-T (green bars). As expected from previous studies, treatment with MβCD or δ-T, but not α-T, relieved NPC1-associated cholesterol storage defects, as indicated by reduced LysoTracker Red staining. *indicates $p<0.0001$ (Student's t-test); error bars=standard deviation. MβCD (Sigma-Aldrich, St. Louis, Mo. cat. #C4555) was resuspended in sterile $H_2O$ to a 1 mM stock solution, while α-T and δ-T were dissolved in DMSO to 40 µM, therefore the untreated controls were no drug added for methyl-β-cyclodextrin treatment, and DMSO only added for α-T and δ-T treatment. Statistical analyses performed using Prism (GraphPad).

The present example tests if biochemical alterations in somatically-derived dermal fibroblasts from NPC1 patients correlated with age of disease onset. Cultured fibroblasts were analyzed for intensity of staining with LysoTracker, a modified fluorophore that is highly selective for acidic cellular compartments, including lysosomes. NPC1 patient fibroblasts exhibited microscopically visible increases in LysoTracker staining compared to control NPC1+/+fibroblasts (FIG. 7A). Quantification of this observation using FACS analysis to measure the fold-change in LysoTracker staining (over background fluorescence of unstained cells) for each fibroblast line showed significantly elevated LysoTracker staining in NPC1 patient fibroblasts ($p<0.0001$) with a large degree of variation; the staining intensity of these cells was 12.65±8.6, while that of controls was 4.41±0.77 (mean±s.d.; FIG. 7B). A statistical power post-test (http://statpages.org/postpowr.html) indicated that the large difference between NPC1 patient and control cells gave a power of 84%, confirming the validity of these results from a relatively small sample size. This increased LysoTracker staining was associated with defective NPC1, as it was lessened by genetic rescue that was achieved via transfection of normal NPC1 cDNA as well as by administration of either methyl-β-cyclodextrin or δ-tocopherol, two compounds previously identified as alleviating NPC1-associated biochemical defects [5-7] (FIGS. 8 and 9).

It was next investigated if the levels of fibroblast LysoTracker staining correlated with any NPC1 disease clinical or genetic parameters. LysoTracker staining did not correlate with the clinical measurement of each patient's disease severity, nor was there correlation between disease severity and the predicted severties of the many various NPC1 mutations represented in this cohort, which were calculated using the MutPred algorithm FIG. 10 and Tables 1 and 2, shown below.

TABLE 1

Linear regression analyses comparing LysoTracker Red staining and quantifiable NPC1 disease parameters.

| Quantifiable Disease Parameter | Number of patients | $R^2$ value | Slope | p value (deviation of slope from 0)[a] |
|---|---|---|---|---|
| Predicted NPC1 Mutation Severity[b] | 15 | 0.003 | −0.009252 ± 0.04554 | p = 0.84 |
| Clinical Severity Score at entry | 27 | 0.06 | −0.2384 ± 0.1832 | p = 0.20 |
| Systemic Age of Onset | 27 | 0.42 | −0.2062 ± 0.04822 | *p = 0.0002* |
| Neurological Age of Onset | 27 | 0.61 | −0.4921 ± 0.07875 | *p < 0.0001* |

[a]Bold/italic font indicates statistical significance, p ≤ 0.05
[b]For details of mutation severity prediction, see Table 2

TABLE 2

Cell lines, mutations and MutPred interpretations from patient fibroblasts.

| Cell | cDNA Mutation[a,b] | Predicted Protein Mutation[a,b] | Mutpred Interpretation[c] | Total Score[d] |
|---|---|---|---|---|
| NPC-4 | c.3182T > C, c.3182T > C | I1061T/I1061T | High Risk/High Risk | 6 |
| NPC-11 | c.3439G > T, c.3742__3745delCTCA | G1146V | */* | * |
| NPC-12 | c.1211G > A, c.3557G > A | R404Q, R1186H | Very High Risk/High Risk | 7 |
| NPC-13 | 6 poss. cDNA changes, c.3662delT | F842L, F1221SfsX20 | */* | * |
| NPC-15 | c.2312__2315delACCT, c.2974 G > C | Unk, G992R | */* | * |
| NPC-18 | c.2474A > G, c.289__291dupTGT | Y825C, 97dupC or 97insC | Medium Risk/* | * |
| NPC-19 | 1920delG, c.1554 - 1009G > A | fs(exon12), IVS9 - 1009G > A | */* | * |
| NPC-20 | 1920delG, c.1554 - 1009G > A | fs(exon12), IVS9 - 1009G > A | */* | * |
| NPC-22 | c.2932C > T, c.3246 - 2A > G | R978C, IVS21-2 A > G | High Risk/* | * |
| NPC-24 | c.3182T > C, c.3182T > C | I1061T/I1061T | High Risk/High Risk | 6 |
| NPC-25 | c.2979dupA| C2103C > G | fs(exon 20), N701K | */* | * |
| NPC-26 | c.3176G > A, c.3742__3745delCTCA | R1059Q, fs(exon24) | High Risk/* | * |
| NPC-34 | c.57 + 1G > T, Unk | IVS2 + 1G > T, Unk | */* | * |
| NPC-37 | hom. c.2201G > T | hom. S734I | High Risk/High Risk | 6 |
| NPC-42 | c.743 G > T, 3410__3411 insA | G248V, fs (exon 22) | Low Risk/* | * |
| NPC-47 | hom. c.3182T > C | hom. I1061T | High Risk/High Risk | 6 |
| NPC-48 | c.1211G > A, c.2861C > T, c.1123A > G | R404Q, S954L, T375A | Very High Risk/High Risk | 7 |
| NPC-50 | c.3182T > C, c.3019C > G or C > T | I1061T, P1007A | High Risk/Very High Risk | 7 |
| NPC-51 | c.3182T > C, c.3019C > G or C > T | I1061T, F1167C | High Risk/* | * |
| NPC-53 | c.3182T > C, c.2861C > T | I1061T, S954L | High Risk/High Risk | 6 |
| NPC-54 | c.2861C > T, Unk | S954L, Unk | High Risk/* | * |
| NPC-55 | c.3019C > G or C > T | P1007A, Unk | Very High Risk/* | * |
| NPC-56 | c.3182T > C, c.743G > T | I1061T, G248V | High Risk/Low Risk | 4 |
| NPC-57 | c.3565__3566insG, 2008__2011delTGCT | Unk, Unk | */* | * |
| NPC-58 | c.1552C > T, c.2594C > T | R518W, S865L | High Risk/High Risk | 6 |
| NPC-59 | c.1552C > T, c.2594C > T | R518W, S865L | High Risk/High Risk | 6 |
| NPC-60 | c.1211G > A, c.3019C > G | R404Q, P1007A | Very High Risk/Very High Risk | 8 |

[a]Genbank Sequences NM_000271 and NP_000262 used for cDNA and amino acid mutation numbering, respectively.
[b]Unk = no mutation identifed.
[c]* = Risk cannot be predicted by software.
[d]MutPred score: Very High Risk 4; High Risk 3; Medium Risk 2; Low Risk 1.
Total score = sum of MutPred scores for both alleles; these were only given to individuals where interpretation was made for both alleles.

However, LysoTracker staining did show significant correlation with age of onset of systemic disease symptoms (p=0.0002, $R^2$=0.42; FIG. 10 and Table 1), and even greater correlation with the age of neurological symptom onset (p<0.0001, $R^2$=0.61; FIG. 7C, Table 1). When patients were grouped into four previously defined disease classes based upon neurological age of onset, LysoTracker staining in early infantile onset patients differed significantly from all other patients (p<0.0001, 1-way ANOVA-Tukey; FIG. 7D). The mean fold-change in LysoTracker staining in early infantile onset patients was 25.4±8.0 (s.d.), while the respective mean fold-changes of late infantile, juvenile, and adolescent/adult patients were 10.9±4.7, 8.1±2.6, and 7.32±1.1.

The examples described herein demonstrate that lysosomal alterations in NPC1 patient-derived fibroblasts, when quantified by FACS analysis, directly correlate to the time of onset of neurological disease symptoms. Adding this simple, inexpensive assay to the testing regimen given to individuals diagnosed with NPC1 could for the first time provide crucial information about disease progression. As the NPC1 field moves towards diagnosis prior to the onset of neurological symptoms [1,2,8], including NPC1 disease identification as a part of newborn genetic screening or in patients with splenomegaly, the addition of this somatic cell assay could provide great assistance for patients and their families in preparation for future life as well as improved disease management by their physicians.

Similar quantitative somatic cell alterations measured by LysoTracker staining may also be informative regarding systemic phenotypes for the >50 additional human lysosomal storage disorders exhibiting lipid accumulation in the lysosome [2,9]. Furthermore, as the defects in somatically-derived fibroblasts directly correlate with CNS-associated neurological symptoms, LysoTracker analysis of patient-derived somatic cells could be used to analyze genetic components that contribute to time of onset and severity of neurological disease, such as genomic analyses of variants that modify inherent lysosomal abnormalities, as well as a first screen for assessing efficacy of compounds in ameliorating the disease symptoms. For example, we recently demonstrated that treatment of fibroblasts with 40 μM δ-tocopherol reduced lysosomal storage defects (including LysoTracker staining) in NPC1, NPC2, Wolman, Batten, Fabry, Farber, Niemann-Pick A, Sanfilippo type B, and Tay-Sachs diseases [1,5].

Importantly, this novel ability to correlate a non-invasive somatic cell assay with cell autonomous neurodegenerative phenotypes may enable accurate prediction of the neurological disease progression of NPC1 disease, and this ability could be extended to other neurode-generative disorders. Recent links between Parkinson disease and lysosomal function [3,10] open the possibility that the somatic cell analysis described herein may be broadly applicable to many neurodegenerative disorders.

Methods

The foregoing Examples were carried out with, but not limited to, the following methods and materials.

Cells and Patient Data

Dermal fibroblasts and clinical data from 27 NPC1 patients were obtained as part of a NICHD, National Institutes of Health, Institutional Review Board-approved NPC1 Natural History study (NCT00344331). Age of disease onset ranged from neonate to 39 years old, and clinical severity score was calculated as previously described [4] when patients entered into the study. Age of systemic onset was considered the age when patients first developed any symptoms, including those of non-neurological origin. Categorization of patients based on age of onset of their neurological symptoms was per current clinical guidelines [2,3]. Four control human fibroblast lines were purchased from Coriell Cell Repository. Culture conditions were as previously described [5] with additional supplementation of 2 mM L-glutamine.

FACS and LysoTracker Red Dye Staining

Cells were plated onto 60 mm tissue culture dishes and cultured to 70-80% confluency. Media were replaced 24 h prior to analysis. On the day of analysis, cells were incubated at 37° C. for 30 min in fresh media containing 1 µM LysoTracker Red dye (LysoTracker) in 3 mL medium/60 mm dish. Cells were then given two PBS washes, trypsinized, pelleted and resuspended in 500 µL medium. FACS data were collected on 10,000 cells using a FACSCalibur (Becton Dickinson Biosciences, Franklin Lakes, N.J.) equipped with Cell Quest software and analyzed using FlowJo (Tree Star). Fold change in LysoTracker staining was calculated as the ratio of geometric means of stained/unstained samples. Duplicate biological replicates were analyzed on three different days, totaling 6 independent samples per cell line.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

[1] M. T. Vanier, G. Millat, Niemann-Pick disease type C, Clin. Genet. 64 (2003) 269-281.

[2] M. T. Vanier, Niemann-Pick disease type C, Orphanet J. Rare Dis. 5 (2010) 16.

[3] M. C. Patterson, C. J. Hendriksz, M. Walterfang, F. Sedel, M. T. Vanier, F. Wijburg, Recommendations for the diagnosis and management of Niemann-Pick disease type C: an update, Mol. Genet. Metab. (2012) 330-344.

[4] N. M. Yanjanin, J. I. Velez, A. Gropman, K. King, S. E. Bianconi, S. K. Conley, et al., Linear clinical progression, independent of age of onset, in Niemann-Pick disease, type C, Am. J. Med. Genet. B Neuropsychiatr. Genet. 153B (2010) 132-140.

[5] M. Xu, K. Liu, M. Swaroop, F. D. Porter, R. Sidhu, S. Firnkes, et al., δ-Tocopherol reduces lipid accumulation in Niemann-Pick type C1 and Wolman cholesterol storage disorders, J. Biol. Chem. 287 (2012) 39349-39360.

[6] A. I. Rosenbaum, G. Zhang, J. D. Warren, F. R. Maxfield, Endocytosis of beta-cyclodextrins is responsible for cholesterol reduction in Niemann-Pick type C mutant cells, Proc. Natl. Acad. Sci. 107 (2010) 5477-5482.

[7] M. Swaroop, N. Thorne, M. S. Rao, C. P. Austin, J. C. McKew, W. Zheng, Evaluation of cholesterol reduction activity of methyl-β-cyclodextrin using differentiated human neurons and astrocytes, J. Biomol. Screen. 17 (2012) 1243-1251.

[8] F. D. Porter, D. E. Scherrer, M. H. Lanier, S. J. Langmade, V. Molugu, S. E. Gale, et al., Cholesterol oxidation products are sensitive and specific blood-based biomarkers for Niemann-Pick C1 disease, Sci. Transl. Med. 2 (2010) 56ra81.

[9] M. L. Schultz, L. Tecedor, M. Chang, B. L. Davidson, Clarifying lysosomal storage diseases, Trends Neurosci. 34 (2011) 401-410.

[10] B. Dehay, A. Ramirez, M. Martinez-Vicente, C. Perier, M.-H. Canron, E. Doudnikoff, et al., Loss of P-type ATPase ATP13A2/PARK9 function induces general lysosomal deficiency and leads to Parkinson disease neurodegeneration, Proc. Natl. Acad. Sci. 109 (2012) 9611-9616.

What is claimed is:

1. A method of diagnosing and treating Niemann-Pick disease in a human subject, the method comprising:
   (a) obtaining a cell sample from a human subject;
   (b) detecting fluorescence in the cell sample of the subject before and after contacting the cell with a detectable probe that accumulates in acidic cellular compartments in the cell;
   (c) calculating the fold-change in fluorescence and comparing it to a reference, wherein the fold-change in fluorescence in the range of 20-35 is predictive of early infantile onset of Niemann-Pick disease, and the fold-change in fluorescence in the range of 5-15 is predictive of late-infantile, juvenile, adolescent, or adult onset of Niemann-Pick disease; and
   (d) administering a therapeutically effective amount of a therapy comprising cyclodextrin to a subject diagnosed with Niemann-Pick disease.

2. The method of claim 1, wherein fluorescence is detected by a Fluorescence activated cell sorter, fluorescence spectroscopy, or microfluorimetry.

3. The method of claim 1, wherein the detectable probe is selected from the group consisting of:

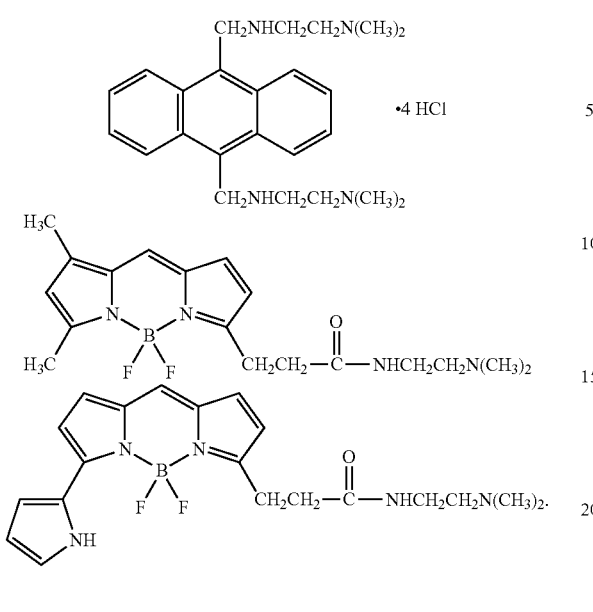

4. The method of claim 1, wherein the detectable probe is

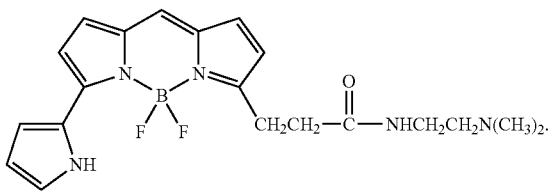

5. The method of claim 1, wherein the cell sample comprises epithelial cells, fibroblasts, or white blood cells.

6. The method of claim 1, wherein the cell sample is obtained in a biopsy or as a blood sample.

7. A method of detecting a fold-change ratio in the range of 5-15 or 20-35 in a subject, comprising:
   (a) obtaining a cell sample from a subject;
   (b) detecting fluorescence in the cell sample of the subject before and after contacting the cell with a detectable probe that accumulates in acidic cellular compartments in the cell;
   (c) calculating the fold-change in fluorescence and comparing it to a reference, wherein the fold-change is either in the range of 5-15 or 20-35.

8. The method of claim 7, wherein fluorescence is detected by a Fluorescence activated cell sorter, fluorescence spectroscopy, or microfluorimetry.

9. The method of claim 7, wherein the detectable probe is selected from the group consisting of:

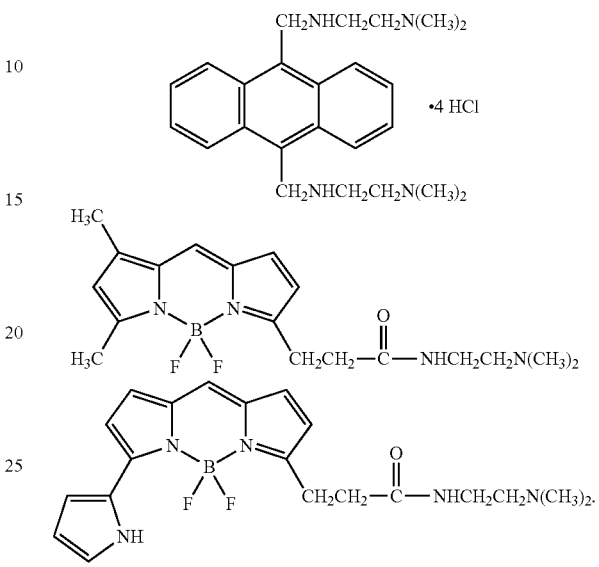

10. The method of claim 7, wherein the detectable probe is

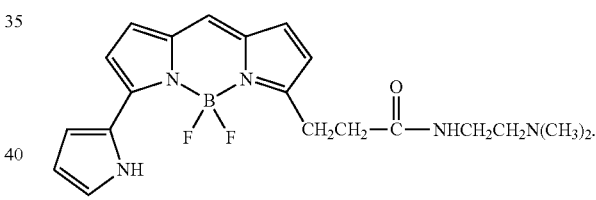

11. The method of claim 7, wherein the cell sample comprises epithelial cells, fibroblasts, or white blood cells.

12. The method of claim 7, wherein the cell sample is obtained in a biopsy or as a blood sample.

* * * * *